(12) United States Patent
Duesing et al.

(10) Patent No.: US 9,318,934 B2
(45) Date of Patent: Apr. 19, 2016

(54) ELECTRIC MOTOR ARRANGEMENT FOR A MEDICAL, ESPECIALLY DENTAL, TOOL HOLDER

(75) Inventors: Josef Duesing, Leutkirch (DE); Alfons Mader, Isny (DE); Johann Stempfle, Pfaffenhofen (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 250 days.

(21) Appl. No.: 13/257,769

(22) PCT Filed: Mar. 19, 2010

(86) PCT No.: PCT/EP2010/053595
§ 371 (c)(1),
(2), (4) Date: Nov. 30, 2011

(87) PCT Pub. No.: WO2010/106157
PCT Pub. Date: Sep. 23, 2010

(65) Prior Publication Data
US 2012/0068557 A1    Mar. 22, 2012

(30) Foreign Application Priority Data
Mar. 20, 2009    (DE) .......................... 10 2009 014 066

(51) Int. Cl.
*H02K 5/08*    (2006.01)
*H02K 9/19*    (2006.01)
(Continued)

(52) U.S. Cl.
CPC .............. *H02K 11/0094* (2013.01); *H02K 5/08* (2013.01); *H02K 5/22* (2013.01); *H02K 9/02* (2013.01); *H02K 9/19* (2013.01); *A61C 1/06* (2013.01); *H02K 7/145* (2013.01); *H02K 2213/03* (2013.01)

(58) Field of Classification Search
CPC .................................. H02K 9/19; H02K 5/08
USPC .................................. 310/43, 52, 54, 58, 59
IPC ....................................................... H02K 9/19
See application file for complete search history.

(56) References Cited

U.S. PATENT DOCUMENTS 4,212,641 A * 7/1980 Eibofner et al. ............... 433/133
4,292,027 A * 9/1981 Richmond .................... 433/127
(Continued)

FOREIGN PATENT DOCUMENTS

DE    3332627 A1    4/1985
DE    10033577 A1 *    4/2001    ............. H02K 29/00
(Continued)

OTHER PUBLICATIONS

Machine Translation, JP 05146107 A, Jun. 11, 1993.*
(Continued)

*Primary Examiner* — Thomas Truong
(74) *Attorney, Agent, or Firm* — Marshall, Gerstein & Borun LLP

(57) ABSTRACT

An electric motor arrangement for a medical, especially dental, tool handle, which is extremely compact and resistant to sterilizing temperatures due to a plurality of advantageous embodiments. The electric motor arrangement is characterized by the following properties: the use of a light source based on SMD-LED or LED as a semiconductor chip; the shortening of the INTRAmatic coupling to between 20 mm and 25 mm; a hermetically extruded stator comprising integrated media tubes and molded connection sockets; the stator winding is embodied as a coil segment winding instead of an H winding or triangle; and the winding head has openings for media tubes.

14 Claims, 14 Drawing Sheets

(51) Int. Cl.
*H02K 7/14* (2006.01)
*H02K 11/00* (2006.01)
*H02K 9/02* (2006.01)
*H02K 5/22* (2006.01)
*A61C 1/06* (2006.01)

(56) References Cited

U.S. PATENT DOCUMENTS

| | | | | |
|---|---|---|---|---|
| 4,406,621 | A | * | 9/1983 | Bailey .......................... 433/126 |
| 4,486,176 | A | * | 12/1984 | Tardieu et al. ............... 433/133 |
| 4,534,732 | A | | 8/1985 | Strohmaier |
| 7,498,711 | B2 | * | 3/2009 | Biais ........................... 310/214 |
| 7,800,259 | B2 | * | 9/2010 | Elgas et al. .................. 310/52 |
| 2004/0001314 | A1 | * | 1/2004 | Bitsche et al. ............... 361/688 |
| 2008/0018180 | A1 | * | 1/2008 | Neal .............................. 310/54 |
| 2008/0252157 | A1 | * | 10/2008 | Muller et al. ................. 310/64 |
| 2009/0004622 | A1 | * | 1/2009 | Kuhn et al. .................. 433/131 |

FOREIGN PATENT DOCUMENTS

| | | | | |
|---|---|---|---|---|
| JP | 05146107 A | * | 6/1993 | .............. H02K 5/08 |
| JP | 2001082390 A | * | 3/2001 | |
| JP | 2004072950 A | * | 3/2004 | .............. H02K 9/19 |

OTHER PUBLICATIONS

Machine Translation, JP 2004072950 A, Mar. 4, 2004.*
Machine Translation, DE 10033577 A1, Apr. 26, 2001.*

* cited by examiner

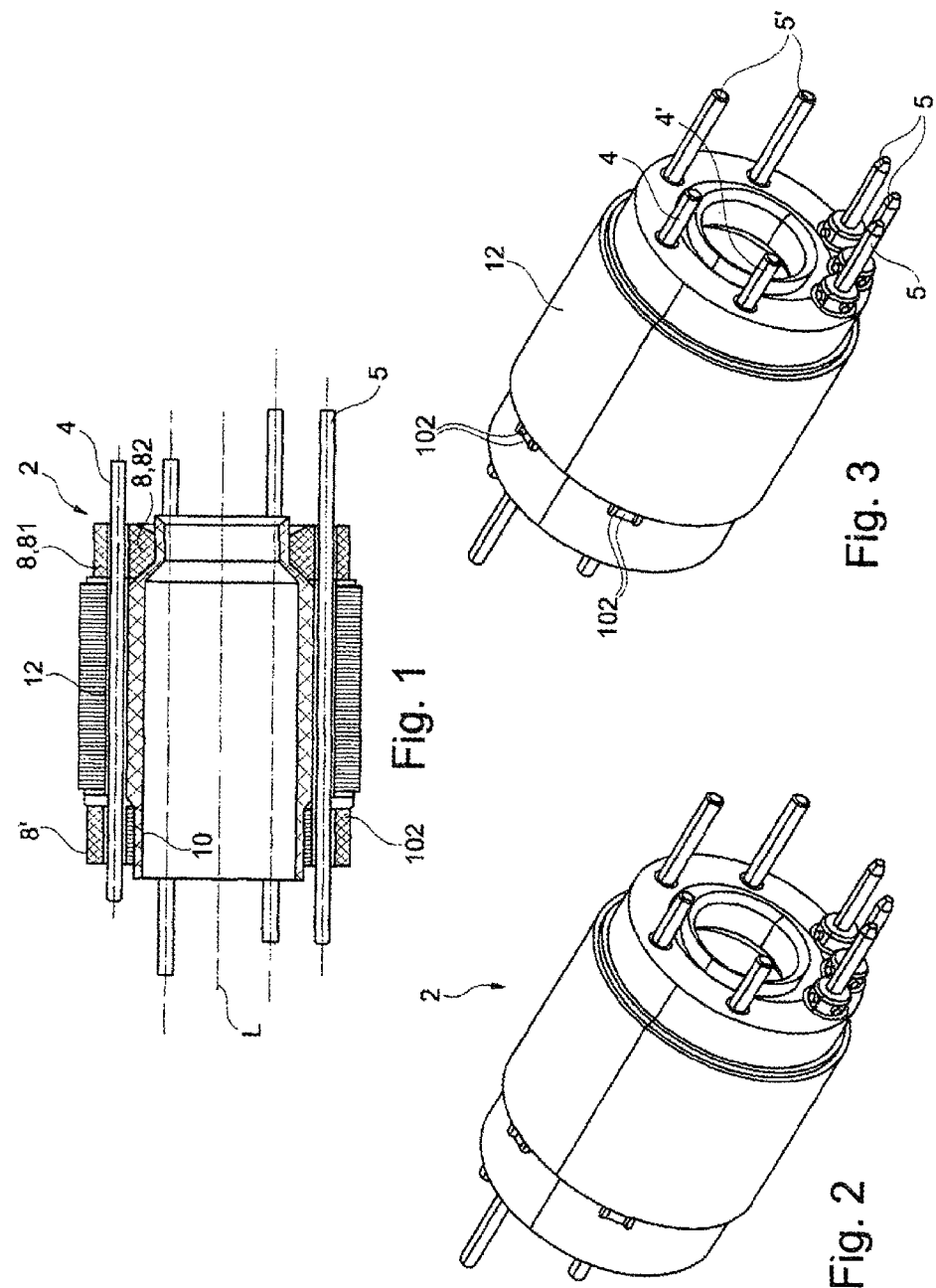

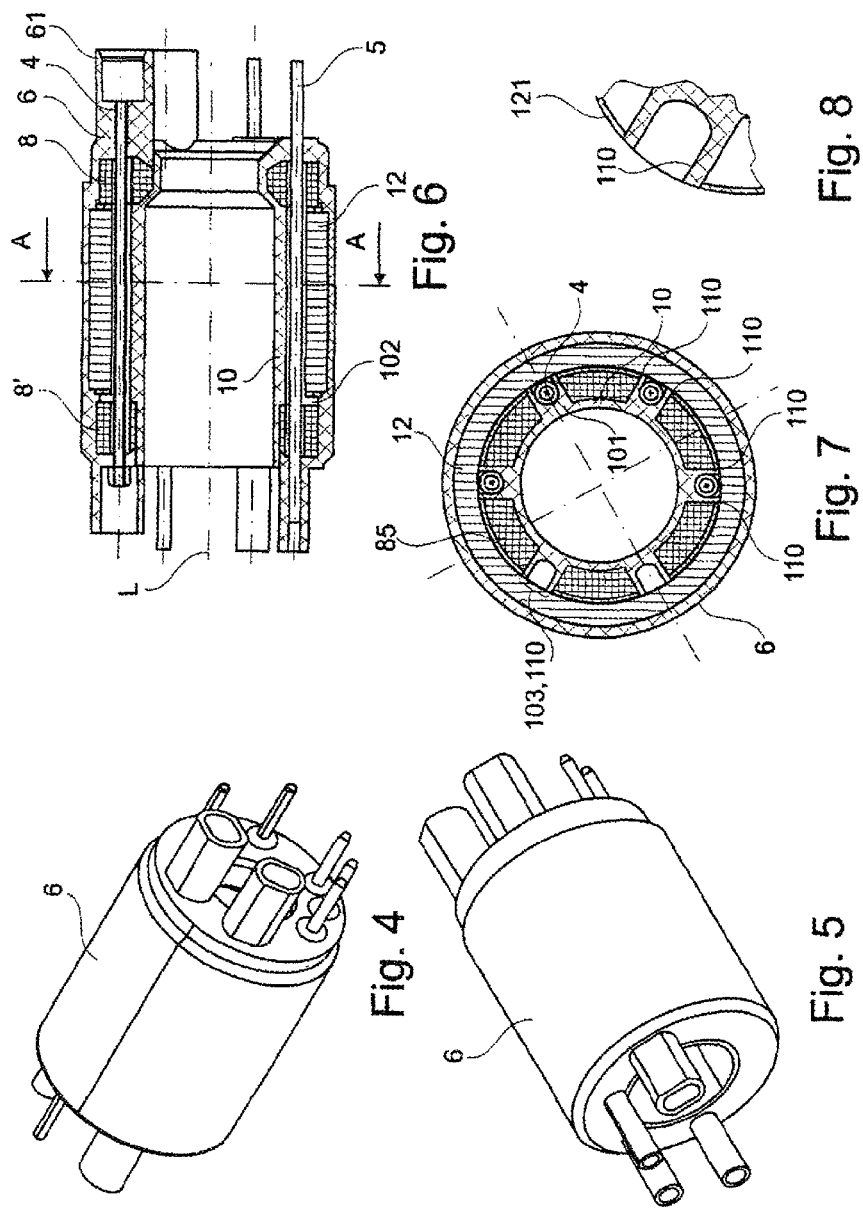

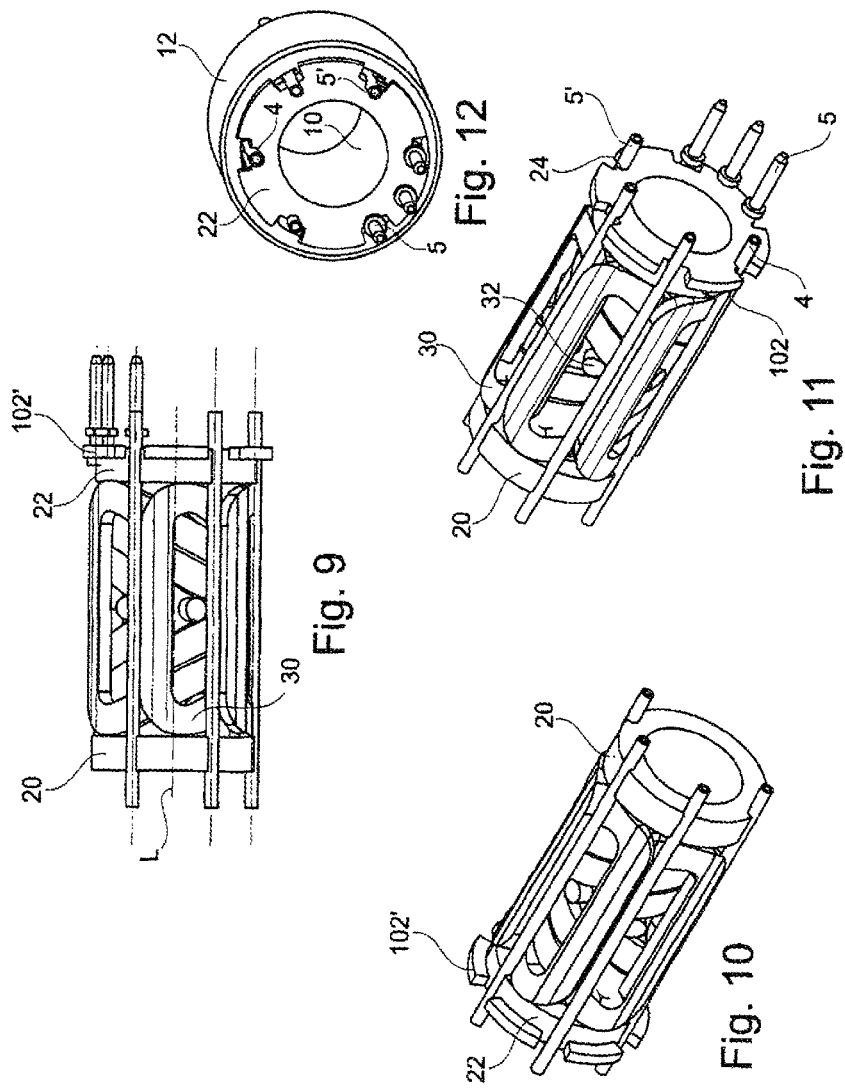

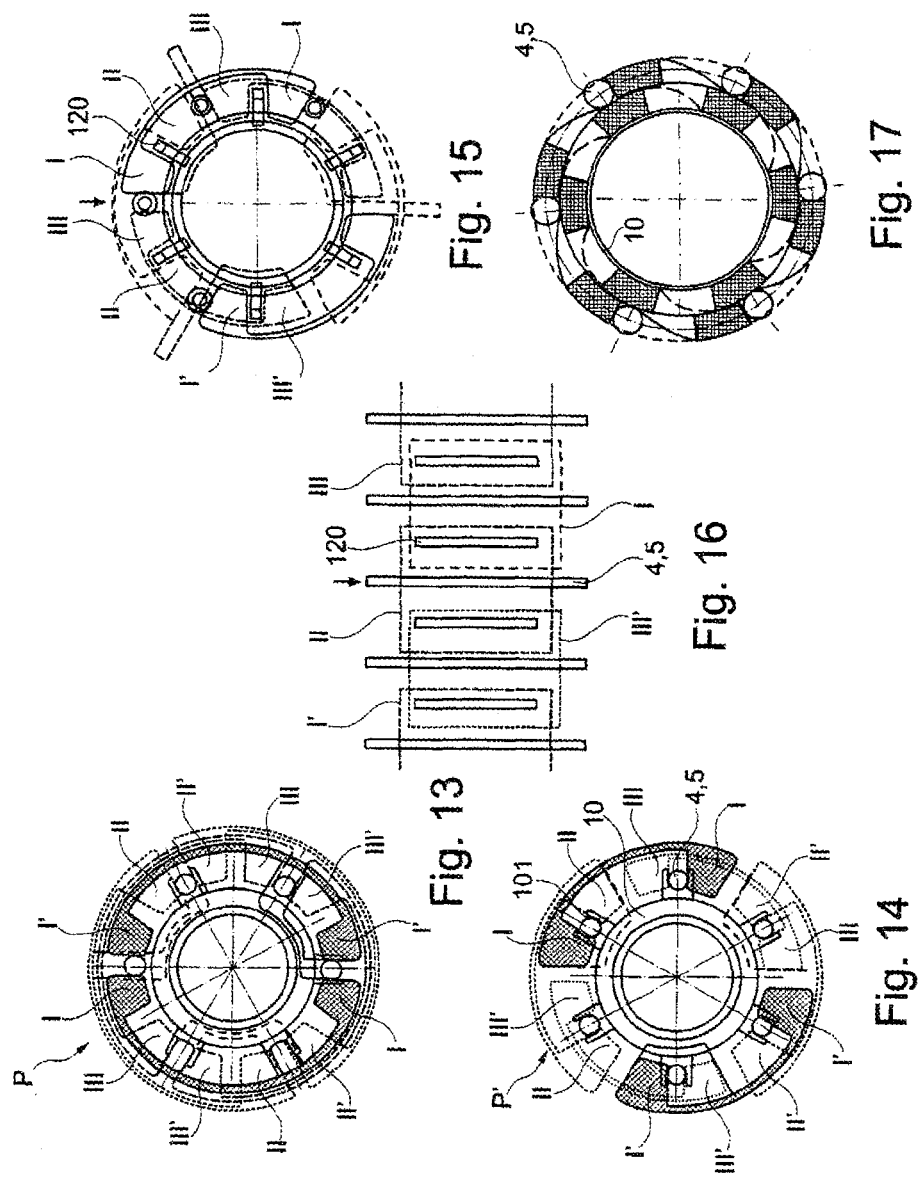

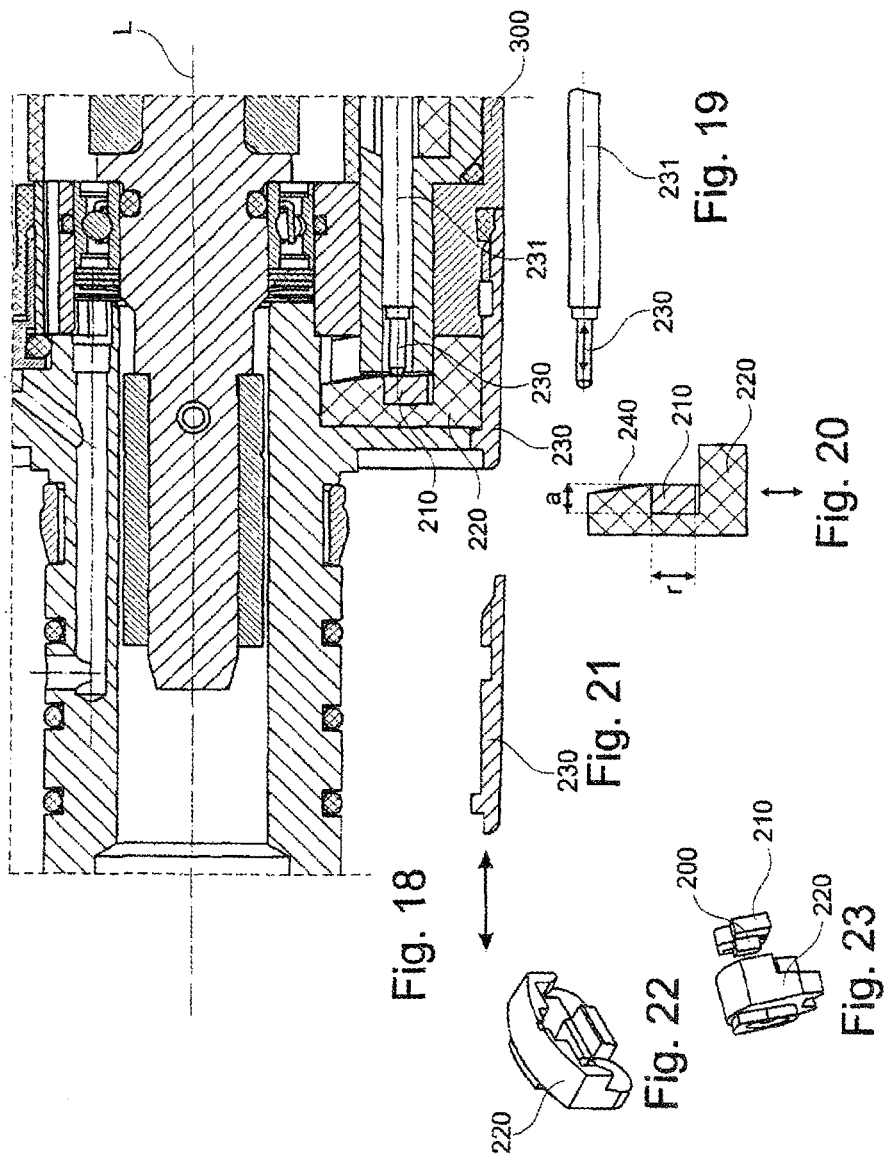

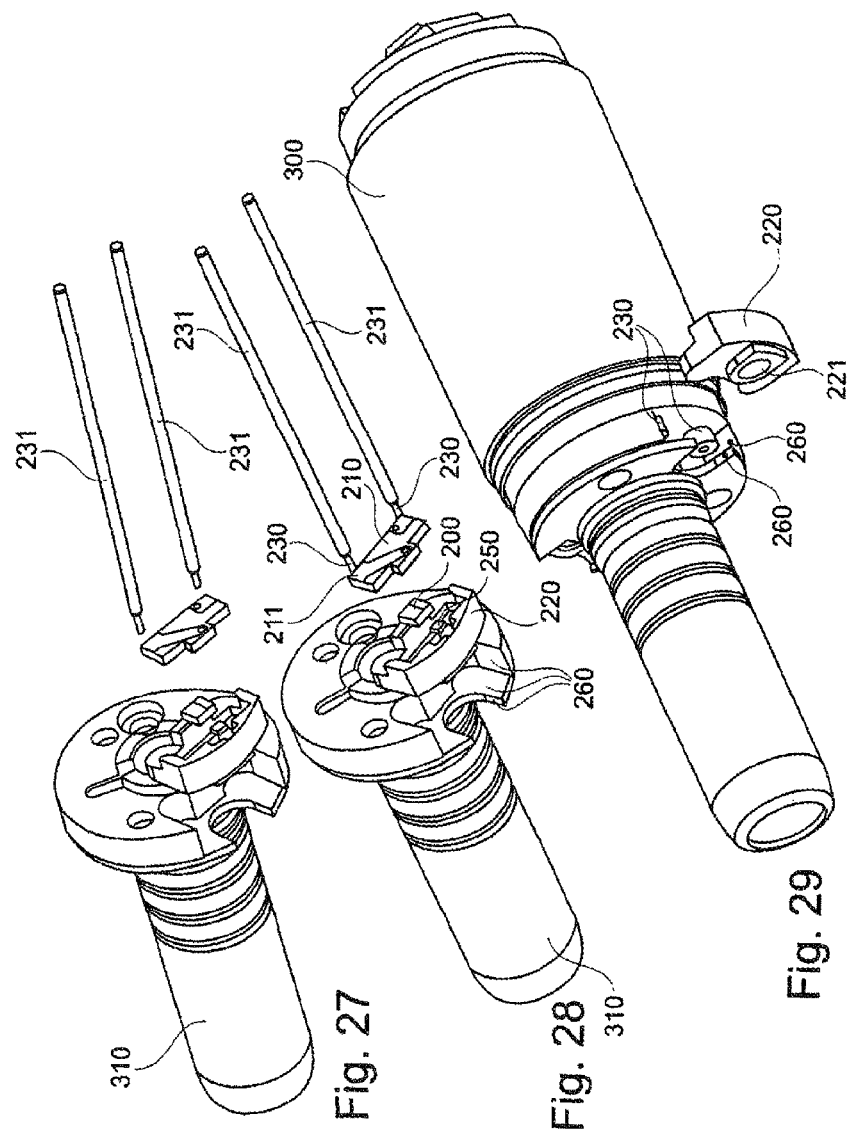

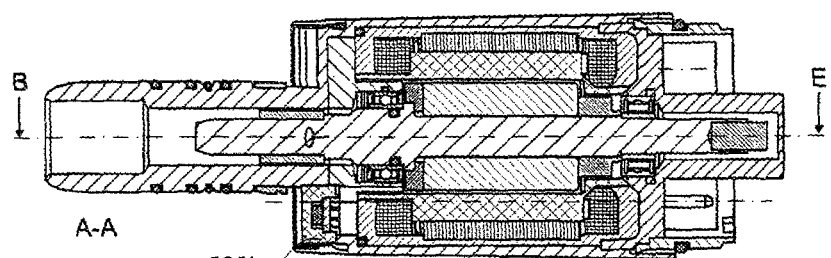
Fig. 30
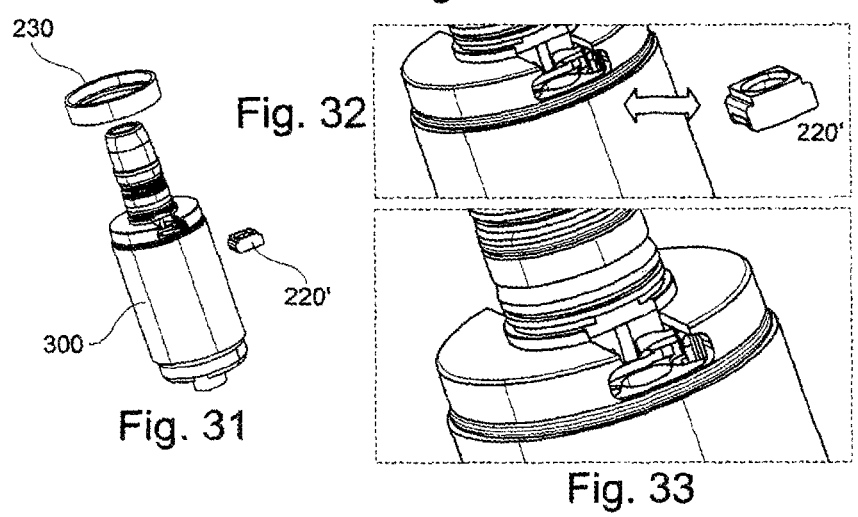
Fig. 31
Fig. 32
Fig. 33
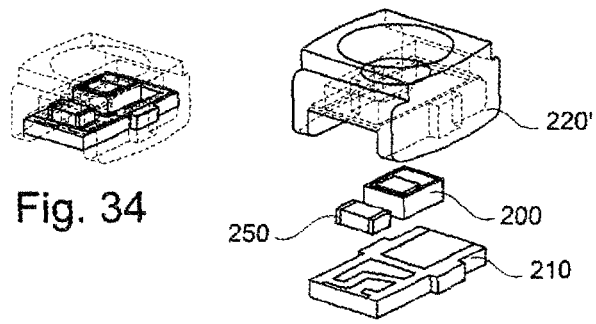
Fig. 34
Fig. 35

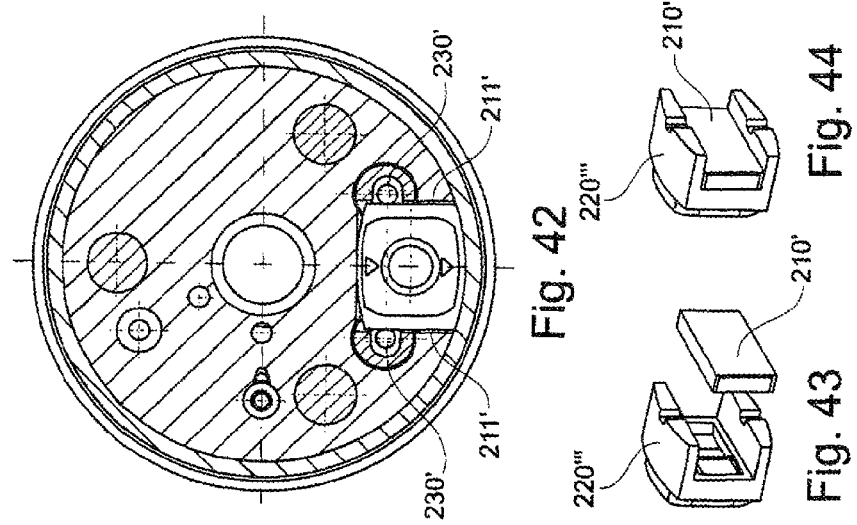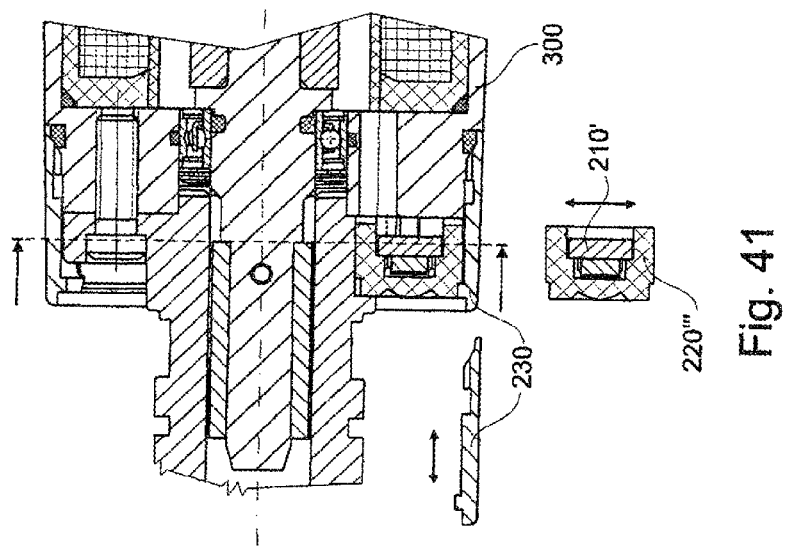

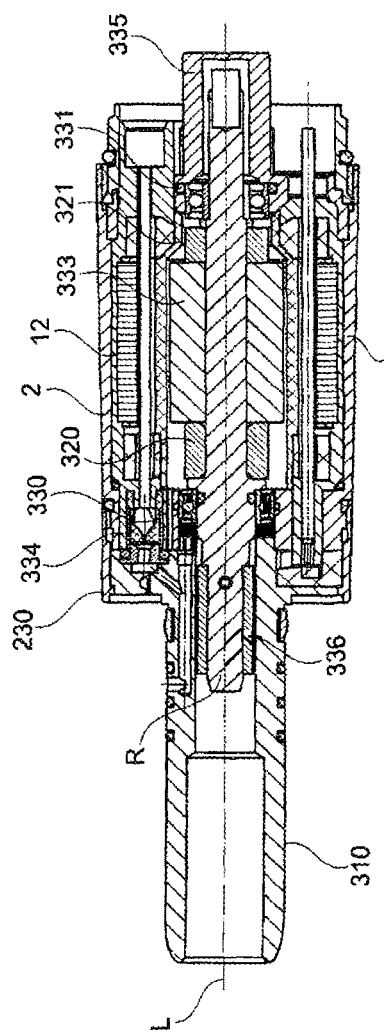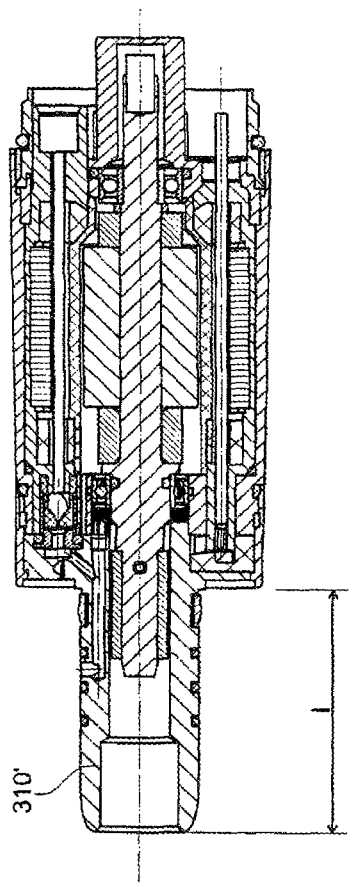
Fig. 45
Fig. 46

ELECTRIC MOTOR ARRANGEMENT FOR A MEDICAL, ESPECIALLY DENTAL, TOOL HOLDER

BACKGROUND OF THE INVENTION

1. Field of the Invention

The present invention relates to an electric motor arrangement for a medical, more particularly dental, handpiece, more particularly a small dental motor, that is to say an electric motor of compact design which is provided more particularly for use in dental handheld devices. Such an electric motor arrangement is also designated hereinafter as "dental motor" or "small dental motor" for short.

2. Related Technology

More particularly, the invention relates to an electric motor arrangement provided for being connected via a coupling to a medical, more particularly dental, handpiece and angular piece, also called "handpiece" for short hereinafter, wherein the handpiece is designed for receiving a rotatably mounted tool, and wherein, when the electric motor arrangement is coupled to the handpiece as intended, a torque generated by the electric motor arrangement can be transmitted to the tool. A corresponding arrangement is known from DE 33 32 627 A1, for example. Furthermore, it can be provided, in particular, that a supply hose is connected by coupling so as to lie opposite the handpiece, with respect to the electric motor arrangement, which supply hose serves to supply the electric motor arrangement or the handpiece and has, for example, medium lines, by which media such as air and/or water for forming a spray can be transported. A power line and/or a light line can also be arranged in the supply hose.

Small dental motors should be sterilized more or less frequently depending on the application. This is being carried out more and more using class B sterilizers. In the course of chamber venting by means of pre-vacuum, the motor is repeatedly exposed to a reduced pressure of up to approximately 50 mbar abs. and alternately superheated steam at 134° C. This sterilization process attacks the insulating enamel of the copper wires, impregnating resins, adhesives and also potting compounds (silicone), used for fixing and protecting the stator winding, to an extreme degree, produces cracks in these materials and breaks down the latter, which ultimately leads to a lack of insulation and an inter-turn fault.

In order to obtain sterilization-resistant motors, it is necessary for the stator to be sheathed completely and impermeably with a sterilization-resistant high-temperature polymer (e.g. PEEK, PPS, LCP, PAI, PPSU, PSU, PES).

The prior art (KL 70/1702) discloses a stator wherein the winding is encapsulated with PPS by injection molding. Six cutouts for the medium line (tubes), from the supply hose connection side to the instrument side or handpiece side are present on the circumference. The magnetic return path is a separate component and not completely encapsulated by injection molding.

In order to obtain the required motor power, the distance between return path and permanent magnet has to be made small. There remains only limited space for the stator encapsulated by injection molding, which has the consequence that the plastic sheathing is made very thin and specifically is not fully closed in the region of the medium line. These imperfections in the plastic enclosure and the return path not encapsulated by injection molding drastically reduce the service life in the case of sterilization using saturated superheated steam and fractionated pre-vacuum.

From the so-called "Chirurgiemotor 550", furthermore, a stator is known wherein a winding head is not sheathed with plastic. The superheated steam attacks the exposed enameled copper wires despite sealing with impregnating resin.

From the so-called system "COMFORTdrive" from the present applicant, a stator is known wherein the coil with enameled copper wires and also the soft-magnetic return path are completely encapsulated by injection molding and contact is made with the individual coil phases by means of contacts injection-molded tightly in the stator body. The medium tubes and the optical fiber rod for guiding light are situated outside the stator body encapsulated by injection molding in a segment-like cutout of the stator, which results in an asymmetrical stator body.

Furthermore, for ergonomic reasons it is desirable to be able to design a corresponding electric motor arrangement as compactly as possible or with a particularly small structural size. As low a weight as possible is also desirable against this background.

SUMMARY OF THE INVENTION

In accordance with a first aspect, the invention is based on the object of specifying an electric motor arrangement for a medical, more particularly dental, handpiece, which electric motor arrangement is sterilization-resistant and in this case enables a particularly compact design of the handpiece.

The first aspect of the invention provides an electric motor arrangement for a medical, more particularly dental, handpiece, having a rotor with a rotor shaft, and also a stator, which is arranged around the rotor with respect to the rotor shaft; moreover, the electric motor arrangement has a medium tube for guiding a medium through it. Furthermore, the electric motor arrangement has a sheath element formed by encapsulation by injection molding, this sheath element, with respect to the rotor shaft, surrounding both the stator and the medium tube tightly in a closed manner in a ring-shaped manner from outside.

By virtue of the sheath element, the electric motor arrangement can be configured in a sterilization-resistant fashion. By virtue of the fact that the medium tube is also surrounded from outside by the sheath element, in this case a particularly compact design of the electric motor arrangement is made possible, which then enables the corresponding handpiece to be designed particularly compactly.

Preferably, the sheath element consists of a high-temperature polymer. Such a material is particularly well suited to the protection of the stator in the case of sterilization.

Preferably, the stator furthermore has a stator winding, wherein a first part of the stator winding, with respect to the rotor shaft, is arranged radially outside the medium tube, and a second part of the stator winding radially inside. In this way, the medium tube can be integrated as it were into the stator, thereby enabling a particularly small-scale design of the stator, more particularly with respect to its radial extent.

Preferably, the sheath element extends beyond the stator on both sides as viewed along the rotor shaft. In this way, the sealing and thus the protection of the stator, more particularly in the case of sterilization, can furthermore be improved. Here the sheath element furthermore advantageously surrounds the medium tube in each case directly in a ring-shaped manner on both sides of the stator. More particularly, it can be provided here that an introduction funnel for the medium tube is formed by the sheath element.

Preferably, the stator has a tubular coil former, which, with respect to the rotor shaft, forms a radially inner boundary of the stator, wherein the sheath element is arranged in a manner directly adjoining the coil former. This enables particularly good and secure sealing.

The coil former preferably has a holding element, more particularly a latching element, for fixing the medium tube. What is made possible in this way for the production of the electric motor arrangement is that, before the formation of the sheath element, the medium tube is simply brought into the intended relative position with respect to the coil former, and is held in position there by the holding element, and the sheath element is subsequently formed by encapsulation by injection molding. This facilitates the production of the electric motor arrangement. In this case, the coil former furthermore advantageously has at least one rib facing radially outward, wherein the holding element is formed at the rib.

Preferably, the stator furthermore has a tubular return path element, wherein the coil former has an abutment element for positioning the return path element along the rotor shaft and/or a centering element for centering the return path element with respect to the rotor shaft. This also facilitates production. If appropriate, the abutment element and/or the centering element can be formed at the rib.

Preferably, the stator has a stator winding embodied in the form of a segment winding over 60°. This enables a winding head formed by the stator winding to be made smaller, so that overall the stator can be made smaller, more particularly in a radial orientation.

A second aspect of the invention relates to an electric motor arrangement for a medical, more particularly dental, handpiece, including a light source.

The length of a dental motor and respectively of a dental motor together with a handpiece to be connected thereto are crucial for the ergonomics of the instrument thus formed overall and for fatigue-free working. In this case, "length" shall be taken to denote the extent of the dental motor along the shaft of the dental motor, that is to say the rotor shaft. Primarily long instruments wherein the center of gravity and the connection point for the supply hose project beyond the bearing area on an operators hand are disadvantageous. Therefore, the aim is to develop a short dental motor.

A light source in a dental motor usually consists of a high-pressure/halogen lamp. The latter extends on the outer circumference of the motor in an axial direction and with its length (approximately 11 mm plus the length of an associated socket) determines the length of the dental motor to a not insignificant degree. Light emitted by the light source is coupled into an optical fiber rod in the handpiece and used in the latter to illuminate a processing location.

When a halogen lamp is incorporated, a considerable space requirement is needed owing to the design and exchangeability, which adversely influences the length of the dental motor. Therefore, in accordance with the prior art, exchangeability is dispensed with or exchangeability is achieved with a mount and contact-connection in the axial direction of the motor, in which case, however, the structural length is then once again influenced adversely.

In accordance with the second aspect, the invention is based on the object of specifying an electric motor arrangement for a medical, more particularly dental, handpiece, having a light source, wherein the electric motor arrangement can be made particularly compact.

In accordance with the second aspect of the invention, an electric motor arrangement for a medical, more particularly dental, handpiece is provided, having a rotor with a rotor shaft, which is mounted in a manner rotatable about a longitudinal axis, and also a light source. In this case, the light source has an LED arranged on a carrier element for electronic components, for example on a flat circuit board, wherein the carrier element is arranged in such a way that its extent with respect to the longitudinal axis in a radial direction is greater than its extent in the axial direction.

An LED can be made significantly smaller than a high-pressure/halogen lamp; by virtue of the said orientation of the carrier element, the electric motor arrangement can thus be made shorter. The LED can be, in particular, an SMD-LED (SMD: surface mounted device).

Preferably, a series resistor for limiting a current flowing through the LED is additionally arranged on the carrier element. The LED can thereby be prevented from overheating. Moreover, it is thereby possible to alter an illuminance of the light emitted by the LED, for example for adaptation to different supply voltages in diverse drive units.

Preferably, the carrier element or the circuit board has a printed circuit board substrate consisting of ceramics or filled plastics. As a result, the carrier element or the circuit board can be designed with good thermal conductivity, as a result of which effective cooling of the LED is fostered or supported.

Preferably, the carrier element or the circuit board has through-holes designed for guiding a cooling air through them. In this way, particularly effective cooling of the LED can be obtained. By way of example, the electric motor arrangement can be embodied in such a way that the through-holes are suitable for guiding through them a cooling air provided for cooling the electric motor.

The electric motor arrangement furthermore preferably has in addition a holding part for retaining the light source, and also a bearing arrangement, by means of which the holding part is mounted in a displaceable manner, preferably mounted in a radially displaceable manner with respect to the longitudinal axis. In this way, the light source can easily be designed in an exchangeable fashion. In this case, the electric motor arrangement furthermore advantageously has a securing element for securing the holding part with respect to a movement along the bearing arrangement.

In particular, the electric motor arrangement can include a motor housing, wherein the bearing arrangement is formed on the motor housing.

Preferably, the holding part has an optical element for optically influencing a light emitted by the light source, for example in the form of a focusing lens. The light emitted by the LED can thereby be guided into an optical waveguide of the handpiece effectively and in a space-saving manner.

The electric motor arrangement furthermore advantageously has a resiliently mounted contact pin for making electrical contact with the light source, wherein the holding part and/or the carrier element have/has an oblique area and the electric motor arrangement is configured in such a way that, in the case of a movement of the holding part along the bearing arrangement, the contact pin is pressed counter to its resilient mounting by the oblique area. This enables particularly good electrical contact-connection and particularly simple handling when the light source is changed.

Preferably, the bearing arrangement and the holding part are embodied in such a way that the holding part can be inserted into the bearing arrangement from outside in two different orientations and can be subsequently displaced as intended along the bearing arrangement. In this way, the arrangement can be designed so that the LED, in the case of incorrectly polarized contact-connection, can be brought to the correct contact-connection with particularly simple handling.

A third aspect of the invention relates to the configuration of a coupling between a corresponding electric motor arrangement and a handpiece, more particularly a coupling element of this coupling, which is part of the electric motor arrangement.

The so-called "INTRAmatic coupling" known for this purpose from the prior art substantially corresponds to the ISO 3964 standard. In this case, the electric motor arrangement has for the purpose of coupling as a coupling element a coupling pin extending in the longitudinal direction of the rotor shaft. With the handpiece coupled, this coupling pin projects far into the handpiece and significantly determines the total length of the instrument formed by the electric motor arrangement and the handpiece.

In order to obtain an ergonomically well-designed instrument, it is necessary for the electric motor to bear as far as possible on the hand support area and to project only insignificantly beyond that with its supply hose connection.

In accordance with the third aspect, the invention is based on the object of specifying an electric motor arrangement for a medical, more particularly dental, handpiece, which electric motor arrangement enables a shorter design of an instrument formed by the electric motor arrangement and the handpiece coupled thereto.

The third aspect of the invention provides an electric motor arrangement for a medical, more particularly dental, handpiece, having a rotor with a rotor shaft, which is arranged so as to be rotatably mounted about a longitudinal axis, and a coupling pin for connection to the handpiece; in this case, the coupling pin has in the direction of the longitudinal axis a length of less than 35 mm, preferably less than 30 mm. In Other respects the coupling pin can be embodied according to the INTRAmatic coupling or in accordance with the ISO 3964 standard.

As a result, the length of the instrument formed from the electric motor arrangement and the handpiece coupled thereto can be made shorter.

In addition, an electric motor arrangement for a medical, more particularly dental, handpiece may be provided, having a rotor shaft rotatably mounted about a longitudinal axis by means of two bearings, and a motor housing consisting of one piece, the motor housing surrounding the two bearings radially from outside with respect to the rotor shaft; the electric motor arrangement furthermore includes a coupling pin for connection to the handpiece. In this case, the coupling pin and the housing are embodied in integral fashion.

As a result, the electric motor arrangement can be made shorter. In addition, an undesired inclination of the coupling pin with respect to the longitudinal axis can be avoided or at least reduced in this way. This is advantageous for torque transmission from the electric motor to the tool arranged in the handpiece.

The three aspects of the invention can advantageously be combined with one another. Therefore, more particularly, an electric motor arrangement is also proposed which comprises those features which are presented in connection with the first aspect and/or those features which are presented in connection with the second aspect and/or those features which are presented in connection with the third aspect.

BRIEF DESCRIPTION OF THE DRAWINGS

The invention is explained in greater detail below on the basis of exemplary embodiments and with reference to the drawings, in which:

FIG. 1 shows a schematic longitudinal sectional view of a stator of an electric motor arrangement in accordance with the invention, FIG. 2 shows a perspective view of the stator, FIG. 3 shows a schematic diagram corresponding to FIG. 2, FIG. 4 shows a perspective view of the stator with sheath element, FIG. 5 shows a corresponding view from a different perspective, FIG. 6 shows a schematic longitudinal sectional view through the stator with sheath element, FIG. 7 shows a schematic cross-sectional view through the stator with sheath element in accordance with the marking A-A in FIG. 6, FIG. 8 shows a schematic detail view concerning FIG. 7 showing a variant, FIG. 9 shows a side view of a variant of the stator without return path element, FIGS. 10 and 11 show two views of the stator shown in FIG. 9 without return path element from different perspectives, FIG. 12 shows a view of the stator shown in FIG. 9 (with return path element), FIG. 13 shows a schematic cross-sectional view of a stator wherein a coil winding is embodied in accordance with an H winding and in this case has a wrapping of 180°, FIG. 14 shows a corresponding schematic cross-sectional view wherein, however, the coil winding only has a wrapping of 120°, FIG. 15 shows a schematic cross-sectional view with an arrangement without superimposition of individual turns of adjacent coils, so that balanced coil currents are made possible, FIG. 16 shows a schematic diagram concerning a development in accordance with FIG. 15, FIG. 17 shows a schematic diagram concerning a delta winding, FIG. 18 shows a schematic longitudinal sectional view concerning an electric motor arrangement with a light source, FIG. 19 shows a contact rod for making electrical contact with the light source, FIG. 20 shows a holding part for retaining the light source, FIG. 21 shows a securing element for securing the holding part, FIG. 22 shows a perspective view of the holding part, FIG. 23 shows a view of holding part and printed circuit board in the mutually separated state, FIG. 27 shows a perspective view of individual parts of an electric motor arrangement with a light source, FIG. 28 shows a corresponding schematic diagram, FIG. 29 shows a perspective schematic view of an electric motor arrangement with a light source on a holding part separate from the motor housing, FIG. 30 shows a schematic longitudinal sectional view of an electric motor arrangement with a light source, FIG. 31 shows a perspective view of an electric motor arrangement with a light source in the case of a separated holding part and separated securing element, FIG. 32 shows a detail view from FIG. 31, FIG. 33 shows a further detail view from FIG. 31, FIG. 34 shows a partly transparent schematic diagram of the holding part with the light source, FIG. 35 shows an exploded illustration corresponding to FIG. 34, FIGS. 36 to 38 show a variant of a holding part with light source, FIGS. 41 to 44 show a further variant, FIG. 45 shows a schematic longitudinal sectional view of an electric motor arrangement with a coupling pin in accordance with the so-called INTRAmatic coupling or in accordance with the ISO 3964 standard, FIG. 46 shows a configuration with a coupling pin shortened by comparison.

DETAILED DESCRIPTION

Figure 24:
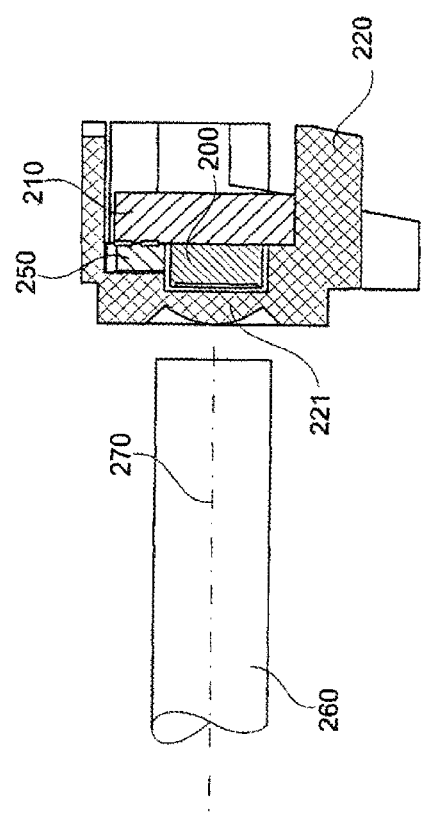
FIG. 24 shows a schematic longitudinal sectional view concerning a variant of the holding part.

FIG. 1 shows a schematic longitudinal sectional view of a stator 2 of an electric motor arrangement in accordance with the invention, FIG. 2 shows a corresponding perspective view of the stator 2, and FIG. 3 shows a schematic illustration corresponding to FIG. 2. The electric motor arrangement furthermore has, as designated for example in FIG. 25, a rotor R having a rotor shaft, the rotor not being shown, however, in FIGS. 1 to 3 for reasons of clarity. The rotor R can be embodied in accordance with the prior art. The rotor shaft is arranged so that it is mounted rotatably; FIG. 1 schematically depicts a longitudinal axis L, which is identical with the axis of rotation of the rotor shaft.

Furthermore, the electric motor arrangement has a medium tube 4. The medium tube 4 is designed to guide a medium, more particularly—viewed in the longitudinal direction of the rotor shaft—from one side of the electric motor arrangement to the opposite side. The medium can be, for example, air and/or water or light or current. The medium tube 4 can extend parallel to the longitudinal axis L of the stator 2.

As can be gathered by way of example from the schematic longitudinal sectional view in FIG. 6, the electric motor arrangement furthermore has a sheath element 6, which is formed by encapsulating the stator 2 by injection molding. The sheath element 6 surrounds both the stator 2 and the medium tube 4 tightly in a closed manner in a ring-shaped manner from outside. This is also apparent from the schematic cross-sectional view in FIG. 7. FIGS. 4 and 5 illustrate two views of the stator 2 with the sheath element 6 from different perspectives.

The sheath element 6 can consist, more particularly, of a high-temperature polymer, for example composed of PEEK, PPS, LCP, PAI, PPSU, PSU or PES. The sheath element 6 serves for protecting the stator 2, more particularly in the case of sterilization.

The stator 2 can have a stator winding, for example in the form of a copper coil, which can form a winding overhang 8 designated for example in FIG. 1, wherein preferably a first part 81 of the stator winding or of the winding overhang 8, with respect to the rotor shaft or the longitudinal axis L, is arranged radially outside the medium tube 4, and a second part 82 radially inside. The medium tube 4 can thereby be integrated as it were into the stator 2, so that overall a particularly compact configuration of the arrangement, in particular in the radial extent, is made possible. As is apparent from FIG. 7, the stator winding can have a section 85 in which the wires of the stator winding are oriented in a manner running parallel to the longitudinal axis L.

As shown for example in FIG. 6, the sheath element 6 can extend beyond the stator 2 to both sides as viewed along the rotor shaft. In this case, particularly good sealing of the stator 2 is possible if the sheath element 6, on both sides of the stator 2, surrounds the medium tube 4 directly in a ring-shaped manner on all sides in a sealing manner. In this case, an introduction funnel 61 for the medium tube 4 can advantageously be formed by the sheath element 6. This facilitates introduction of the medium into the medium tube 4.

The stator 2 can furthermore advantageously have a tubular coil former 10, which, with respect to the rotor shaft, or the longitudinal axis L, forms a radially inner boundary of the stator 2, wherein the sheath element 6 is arranged in a manner directly adjoining the coil former 10. In particular, the sheath element 6 can be formed by encapsulation by injection molding in such a way that it is applied on the coil former 10 during the process of encapsulation by injection molding.

As shown in FIGS. 1 and 6, it can be provided that, as viewed along the rotor shaft or the longitudinal axis L, the two lateral boundaries of the stator 2 are respectively formed by a winding overhang 8, 8', and, outside these two boundaries or winding overhangs 8, 8', the sheath element 6 is arranged on the coil former 10 directly in a sealing manner.

The coil former 10 preferably has a holding element 101, expediently in the form of a latching element, for fixing the medium tube 4. As a result, in particular during the process of encapsulation by injection molding, the medium tube 4 can be held in the intended relative position with respect to the coil former 10.

Furthermore, the stator 2 advantageously has a tubular return path element 12, which preferably surrounds the coil former 10 in a ring-shaped manner. The return path element 12 (also designated hereinafter as "return path" 12 for short) can be formed, more particularly, from a soft-magnetic material. In this case, the coil former 10 can have an abutment element 102—designated by way of example in FIG. 6—for the positioning of the return path element 12 along the rotor shaft or the longitudinal axis L. By way of example, the abutment element 102 can be configured as a longitudinal stop.

Moreover, the coil former 10 can have a centering element 103, which serves for centering the return path element 12 with respect to the rotor shaft or with respect to the longitudinal axis L.

As is the case in the exemplary embodiment shown here, the coil former 10 preferably has a plurality of radially outwardly facing double webs 110, more particularly six thereof, which are designed to be able to act both as holding element 101 for fixing the medium tube 4 and as centering element 103 for centering the return path element 12. Moreover, they can have a radially outwardly facing elevated section, which forms the abutment element 102.

The electric motor arrangement can additionally have at least one further medium tube 4', designated by way of example in FIG. 3, wherein the electric motor arrangement, with respect to the further medium tube 4', is preferably embodied analogously to the embodiment with respect to the medium tube 4 mentioned first.

The electric motor arrangement can additionally have electrical contact rods 5 (also designated hereinafter as contacts 5 for short) for making electrical contact with the stator 2 and/or further electrical contact rods 5' for making electrical contact with a light source, for example an LED (light-emitting diode). The arrangement of the contact rods 5 and of the further contact rods 5' can be configured analogously to the arrangement of the medium tube 4. A contact rod 5, 5' can therefore correspondingly be led through the winding overhang 8, etc.

More particularly, the electric motor arrangement with the stator 2 can be configured in accordance with the following illustration:

In accordance with the first aspect of the invention, it is thus possible to specify a small, hermetically sealed, compact, sterilizable stator 2 wherein, besides copper coil and soft-magnetic return path 12, the medium tubes 4, 4' and the electrical connections 5' for the light source are also encapsulated by injection molding, wherein the medium tubes 4, 4' and electrical connections 5' for the light source are led through the stator winding, and exit from the stator 2 at the end sides thereof, wherein their exit position correlates with the positions of the existing connectors in the supply hose. In this case, the medium tubes 4, 4' and electrical contacts 5 should be completely enveloped by the stator sheath material apart from the connection openings.

For this purpose, a stator 2 is proposed which is configured as follows.

The stator 2 encapsulated with high-temperature polymer (e.g. PEEK, PPS, LCP, PAI, PPSU, PSU, PES) by injection molding forms a compact, impermeable, sterilization-resistant body comprising the motor winding, the soft-magnetic return path 12, the medium tubes 4, 4' and electrical contact rods 5, 5', the internal diameter of which is formed by the coil former 10 and at the end faces of which sockets are formed which are connected to the medium tubes 4, 4', and from the end faces of which the electrical contact rods 5, 5' or electrical contact sockets project.

The embodiment of the coil winding is preferably as follows.

The coil former 10 consists of a sleeve with double separating webs 101 (also designated hereinafter as double-walled separating webs 101) placed on the outer circumference and serving for separating the individual phases in a 60° (3-phase) arrangement. The double separating webs 101 are provided with an elevation that forms an abutment element 102, which predetermines the axial position of the magnetic return path 12. The copper winding is arranged between the double separating webs 101. On the outer circumference, the separating webs 101 support and center the soft-magnetic return path 12.

In a particular embodiment, indicated in FIG. 8, the separating webs 101 are inserted into cutouts of a (plastic) sleeve 121 carrying the soft-magnetic return path 12 and center the return path ring 12 directly at its internal diameter.

The medium tubes 4, 4' and electrical contact rods 5, 5' are arranged within the double separating webs 101. By this means, the supply of the attached instrument or handpiece with spray water and spray air but also the electrical supply of the light source, is effected from the supply hose connection if the electric motor arrangement is connected to the corresponding components.

The medium tubes 4, 4' and/or contact rods 5, 5' are clipped into the double separating webs 101 and oriented before the complete stator 2 is encapsulated by injection molding. In extension of the medium tubes/contact rods 4, 4', 5, 5', on both plane sides of the stator 2, tube-like extensions or cylindrical cutouts are introduced on the stator 2, used firstly for making fluidic and electrical contact with the medium connection in the supply hose and the motor-internal relaying.

The medium tubes 4, 4' and contact rods 5, 5' are preferably embodied straight without a bend and offset. The medium tubes 4, 4' preferably have no separate introduction funnels or sockets at their ends or integrally formed. The introduction funnels 61 or sockets are concomitantly integrally formed directly on the stator body during encapsulation by injection molding.

A variant is conceivable in this case. The winding is applied with single-walled, more solid separating webs. The medium tubes 4, 4' are inserted into the interspaces of two adjoining winding sections and the winding sections are thus held exactly in position including during subsequent encapsulation by injection molding. Therefore, the three phase currents can also be realized in narrower limits, which results in less heating of the motor.

FIGS. 9 to 12 show a variant of the stator 2. The reference signs are used analogously. FIG. 9 shows a side view of the stator 2 with the return path element 12 removed; FIGS. 10 and 11 show corresponding perspective views. FIG. 12 shows a perspective view of the stator 2 with return path element 12.

In this variant, the coil former 10 has two radially outwardly facing ribs 20, 22, which constitute a lateral boundary for the stator winding. The ribs 20, 22 have holding elements 24, preferably in the form of latching elements for fixing the medium tubes 4, 4' and contact rods 5, 5'. On one of the two ribs, on the rib 22 in the case shown, a variant of the abutment element 102' for the longitudinal orientation of the return path element 12 can be integrally formed; this can in turn serve, more particularly, as a mounting aid during encapsulation by injection molding. Furthermore, the ribs 20, 22 can have a centering element or be embodied as such a centering element, which serves for centering the return path element 12.

The stator winding can be embodied as a delta winding; in particular, six delta coils 30 can be provided as the stator winding. More particularly, the following configuration can be provided:

The delta coils 30 are fixed on a tubular coil body or coil former 10 having near the two ends a circumferential rib 20, 22, which has, in 60° pitch, cutouts into which the medium tubes 4, 4' and electrical contact rods 5, 5' are clipped. The delta coils 30 are arranged between the two circumferential ribs 20, 22 and the connections are connected up and provided with contacts. The contacts 5 for the electrical connection of the three motor phases can also be clipped in at least one of the two circumferential ribs 20, 22, preferably in both ribs 20, 22.

For the exact positioning of the delta coils 30, bollards 32 are arranged on the lateral surface of the coil former 10, the delta coils 30 being suspended into these bollards. Alternatively, a bearing edge can be provided for this purpose. The delta coil 30 is situated directly on the lateral surface of the coil former 10 and is integrally formed and baked in this position. The medium tubes 4, 4' are positioned in the edge at the transition from one delta coil 30 to the adjacent coil. These tubes thus lie above the delta coils 30 and hold the latter on the coil former 10.

The centering of the magnetic return path 12 with respect to the core or with respect to the coil former 10 can be effected by means of the medium tubes 4, 4' arranged on the circumference, but is performed more advantageously, in particular more accurately, by means of the two circumferential ribs 20, 22, on which the return path assembly 12 bears and is also held axially by means of a stop 102, for example in the form of a collar or flange. This also prevents a change in the position of the clipped medium tubes 4, 4' during the subsequent process of encapsulation by injection molding.

The completely preassembled stator 2 can therefore be inserted simply into a hot injection molding die: all the connections are pre-fixed and do not have to be laboriously inserted in receptacles in the hot die.

One partial aspect of the electric motor arrangement according to the invention or of the small motor according to the invention relates to the stator. A stator having segment windings for three-phase motors is known which has phase sections which are wound as a coil onto a coil former or which are wound and formed separately as an individual coil e.g. in delta form and are subsequently fixed on a coil former.

In the case of coil windings, the wire loops present at the coil ends are formed into a winding overhang. In the case of the customary H winding, wherein the respective coil section encloses the largest area, in this case three sections lie one above another at the coil ends. This is illustrated in the cross-sectional illustration in FIG. 13; the coil sections are designated by the Roman numerals I, I', II, II', III, III'. It is evident that, by way of example, at the location designated by the arrow P the three coil sections I, III and II are arranged radially one above another, to be precise in this order from the inner position outward. For short, compact motors, these wire loops are formed into a winding overhang. Therefore, a relatively large winding overhang arises in the case of three sections.

Preferably, therefore, the coil winding is embodied as a segment winding over 60° (instead of 120°). This is correspondingly illustrated in FIG. 14. The enclosed area permeated by field lines thus admittedly becomes smaller, but only two sections are superimposed in the winding overhang, as a result of which the winding overhang can be worked more easily and turns out to be significantly smaller. By way of example, at the location designated by the arrow P', only the two coil sections III' and II are arranged radially one above the other, to be precise in this order from the inner position outward. This is particularly advantageous in particular if medium tubes 4, 4' and electrical contact rods 5, 5' are also led through the winding overhang.

These lead-throughs or medium tubes 4, 4' or contact rods 5, 5' can, as shown by way of example in FIG. 14, be arranged analogously to the above illustration in double-walled separating webs 101 extending outward radially from a coil former 10.

However, the medium tubes 4, 4' or contact rods 5, 5' can also be positioned between two adjoining winding sections. This is shown by way of example in FIG. 15; FIG. 16 schematically shows a portion of a development of the arrangement in accordance with FIG. 15. In this case, for easier orientation in each case in FIGS. 15 and 16 a medium tube 4 or contact rod 5 is marked by a small arrow. By way of example, it is evident with reference to FIG. 16 that the medium tube 4 or contact rod 5 marked by the arrow is directly adjoined by the winding section I from the right and the winding section III' from the left.

In the case of arrangement between two winding sections, the medium tubes or contact rods are held exactly in position, without winding wires from adjacent sections being able to overlap and electrical losses arising during the subsequent process of encapsulation by injection molding. In the case of arrangement between the winding sections, the winding overhang can be formed more easily.

The coil former 10 can have, as indicated in FIG. 15, six radially outwardly facing webs 120 arranged so that two adjacent webs 120 in each case form an angle of 60°. The webs 120 can, in particular, extend parallel to the longitudinal axis L and in each case be arranged centrally between two double-walled separating webs 101. In this way, the winding sections can be positioned particularly well. In this configuration, therefore, the medium tubes 4, 4' or contact rods 5, 5' can in each case be arranged centrally between two webs 120.

In the configuration shown in FIG. 15, no superimpositions of individual turns of adjacent coils arise. Therefore, balanced coil currents can form. The gaps between two adjacent coils or winding sections can be filled by medium tubes 4, 4' or contact rods 5, 5'; as a result, the coils or winding sections can be held particularly well in the desired form or position; they lie as it were at the ideal geometrical location.

For comparison, FIG. 17 schematically depicts the arrangement of delta sections, corresponding to the embodiment shown in FIGS. 9 to 11.

An electric motor arrangement with a light source can be made particularly short if the light source has an LED arranged on a carrier element for electronic components, for example on a flat circuit board, wherein the carrier element is arranged in such a way that its extent with respect to the longitudinal axis L in the radial direction is greater than its extent in the axial direction. One exemplary embodiment in respect thereof is schematically depicted in FIGS. 18 to 20. In this case, FIG. 18 shows an excerpt from a schematic longitudinal sectional view with the carrier element 210, here in the form of a flat circuit board. A holding part 220 is expediently provided, which serves for retaining the light source or the LED 200. In particular, the carrier element 210 can be arranged on the holding part 220.

FIG. 20 shows the holding part 220 and the carrier element 210 in a separated state, wherein the orientation with respect to the longitudinal axis L—as indicated symbolically by the double-headed arrow—in accordance with FIG. 18 is maintained. As is apparent from FIGS. 18 and 19, for example, the carrier element 210 is arranged in such a way that its extent with respect to the longitudinal axis L in the radial direction r is greater than its extent in the axial direction a. Preferably, the holding part 220 is also arranged in such a way that its extent in the radial direction is greater than its extent in the axial direction.

Furthermore, a bearing arrangement is expediently provided, by means of which the holding part 220 is mounted in a displaceable manner, preferably mounted in a displaceable manner radially with respect to the longitudinal axis L, that is to say in the direction of the double-headed arrow shown schematically in FIG. 20. Preferably, the bearing arrangement is formed on a motor housing 300 of the electric motor arrangement. More particularly, the bearing arrangement can be configured in such a way that the holding part 220 can be detached from the rest of the electric motor arrangement and can subsequently be introduced again into the bearing arrangement.

Preferably, a securing element 230 is furthermore provided, for example in the form of a ring element, which extends in a ring-shaped manner around the longitudinal axis L and which serves for securing the holding part 220 relative to a movement along the bearing arrangement. The holding part 220 can thereby be fixed in its intended relative position with respect to the rest of the electric motor arrangement.

For making electrical contact with the LED 200, a contact pin 230 is advantageously provided, which is mounted in a resilient manner, for example on a contact rod 231. The contact rod 231 can be embodied, in accordance with the above description with respect to the first aspect of the invention, as a contact rod 5 which is enclosed by the sheath element 6 and thus integrated into the stator 2.

The holding part 220 preferably has an oblique area 240, wherein the electric motor arrangement is configured in such a way that, in the case of a movement of the holding part 220 along the bearing arrangement, the contact pin 230 is pressed counter to its resilient mounting by the oblique area 240. This enables particularly good electrical contact to be made with the LED 200.

FIG. 24 shows a variant; as is apparent from this illustration, the holding part 220 can have an optical element 221, for example in the form of a focusing lens. As a result, light emitted by the LED 200 can be effectively coupled into an optical waveguide 260 which is arranged in the handpiece and which is designed to guide the light to a processing location of the handpiece. The optical element 221 can be configured as an integral part of the holding part 220 or be held by the holding part 220.

The arrangement can be embodied more particularly as represented in greater detail below:

One approach for shortening the length of the dental motor is, therefore, the arrangement of the light source with its main extent transverse with respect to the motor axis or longitudinal axis L. This is preferably realized by means of an SMD-LED 200, which is arranged on a flat printed circuit board or circuit board, the main extent of which is transverse with respect to the motor axis.

The printed circuit board with LED 200 and electrical circuitry possibly required is situated in/on a holding part 220. The holding part 220 has, in extension of the main emission direction of the LED 200, an integrally formed or held optical element 221, which couples the LED light into the optical fiber rod or optical waveguide 260 on the angular piece side. The holding part 220 is inserted radially into a cutout on the motor housing 300 and fixed by a securing element 230 in the form of a screw collar ring.

The SMD-LED 200 is positioned and electrically contact-connected (e.g. by soldering, clamping, conductive adhesive bonding, wire bonding) on a carrier element 210, e.g. in the form of a printed circuit board. In order to avoid overheating, the diode current is limited by a series resistor 250, designated by way of example in FIG. 24. This resistor simultaneously serves for adapting the illuminance to different LED qualities, and also to the different supply voltages in diverse drive units (dental units/control units).

The series resistor 250 is arranged on the same carrier element 210 or on the same printed circuit board as the LED 200. The printed circuit board substrate ideally consists of a material having good thermal conductivity such as ceramic, filled plastic, FR4 with metal inlay as a heat sink, etc. The printed circuit board is preferably provided with through-holes through which a cooling air, more particularly the motor cooling air, can be guided and thus also cools the SMD-LED 200.

The printed circuit board with the components (LED, resistor) soldered thereon is held by a preferably transparent holding part 220, which consists for example of plastic or glass (covered, held), which has in extension of the optical axis 270 of the SMD-LED 200 a focusing lens, via which the LED light is coupled into the optical fiber rod or optical waveguide 260 in the handheld angular piece. The holding part 220 has on the outer contour guide areas used for orienting the complete light source (SMD-LED 200 plus printed circuit board plus holding part 220) in the motor housing 300.

The light source is inserted radially into a cutout provided on the motor housing 300, in the manner of a drawer. A screw collar ring or securing element 230 fixes the light source in the predetermined position. The preferably metallic screw collar ring also prevents the lateral emergence of stray light from the transparent holding part 220.

Contact areas are provided on the underside or a side of the carrier element 210 or of the printed circuit board which lies opposite the LED 200. During radial insertion of the light source into the motor housing 300, resilient contact pins 230 in the motor are tensioned by means of an oblique area 240 or bevel 240 for short on the holding part 220 or on the printed circuit board. These contact pins together with the contact areas on the underside of the printed circuit board constitute the electrical connection to the supply hose connection. The spring contacts 230 are inserted into electrically conductive sleeves connected to the plug contacts on the hose side.

In contrast to a halogen lamp extending along the motor axis, the main extent of the LED light source is transverse with respect to the motor axis. A significant reduction in the length of the dental motor is thus obtained.

Figure 25:
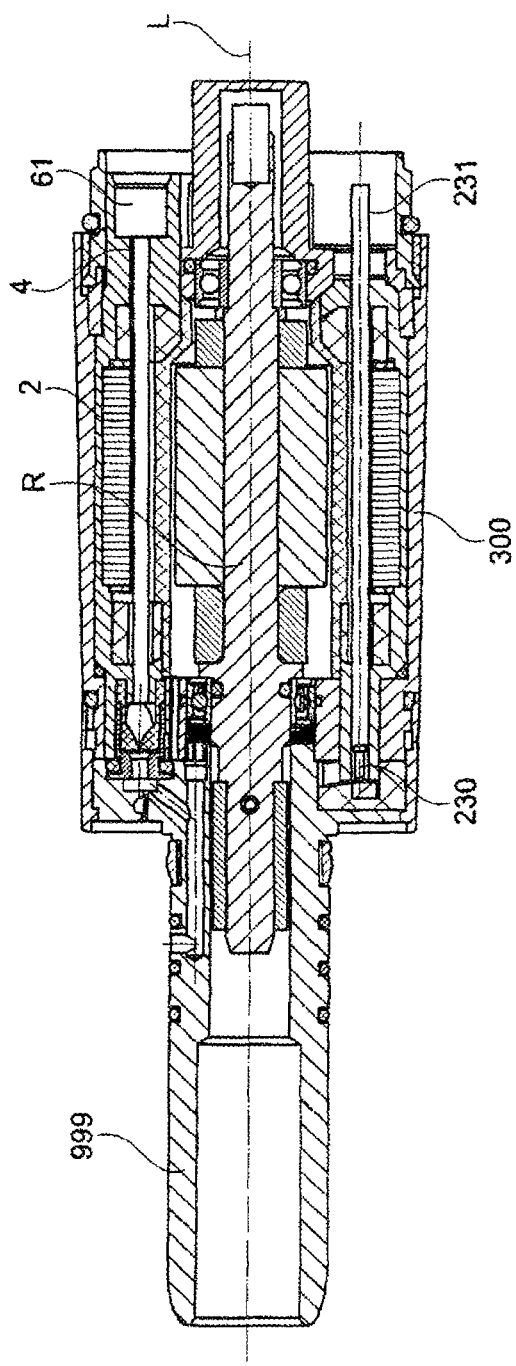
FIG. 25 shows a schematic longitudinal sectional view concerning an electric motor arrangement with a light source.
Figure 26:
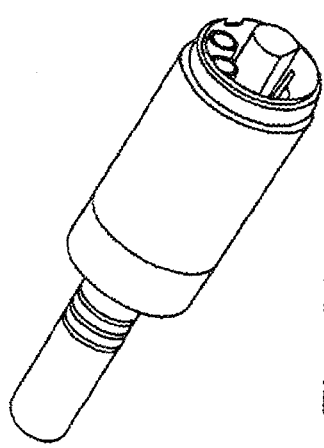
FIG. 26 shows a perspective view of the electric motor arrangement illustrated in FIG. 25.

FIG. 25 shows a schematic longitudinal sectional view of an electric motor arrangement wherein both the first aspect of the invention ("sheath element") and the second aspect of the invention ("LED on carrier element") are realized. Here the rotor R of the electric motor arrangement is designated, being mounted in a manner rotatable about a longitudinal axis L. FIG. 26 shows a corresponding perspective view.

The arrangement in accordance with the exemplary embodiment is illustrated more extensively in perspective form in FIGS. 27 to 29. In this case, two contact rods 231 can be discerned, and accordingly two resiliently mounted contact pins 230 for making electrical contact with the LED 200. The reference sign 211 designates contact areas formed on the carrier element 210 for making contact with the contact pins 230.

The reference sign 260 designates a cutout formed in the motor housing 300 for receiving the holding part 220.

The reference sign 310 designates a coupling pin embodied as a coupling element for connection to the handpiece.

An LED has to be operated with a specific polarity. In the case of incorrect polarity, the chip LED does not emit light, or a parallel-connected protective diode present, if appropriate, emits red light. Dental units and drive devices are installed in large numbers and with great variance in the field. The polarity for the instrument illumination is not defined in this case. In order to enable a user of the electric motor arrangement to reverse the polarity of the LED 200 in a manner that is easy to carry out, the bearing arrangement and the holding part 220 are preferably embodied in such a way that the holding part 220 can be introduced into the bearing arrangement from outside in two different orientations and can subsequently be displaced along the bearing arrangement in the manner intended. As a result, the arrangement can be designed so that, in the case where contact is made with the LED 200 with incorrect polarity, the correct polarity can be established by changing the orientation of the holding part 220.

By way of example, the arrangement can be designed so that the holding part 220 can be separated from the rest of the electric motor arrangement by displacement along the bearing arrangement, can then be rotated by 180° and can be inserted into the bearing arrangement again in the orientation newly assumed in this way, until contact has been made in the corresponding other polarity.

FIGS. 30 to 35 illustrate a variant in accordance with this configuration. FIG. 30 shows a schematic longitudinal sectional view, FIG. 31 a perspective view and FIGS. 32 and 33 details from FIG. 31. In particular, the securing element 230 in the form of a screw collar ring and the holding part 220' in accordance with this variant can be discerned. As is apparent from FIG. 32, for example, the holding part 220' is embodied in symmetrical fashion, so that it can be inserted into the bearing arrangement in the motor housing 300 in two different orientations, wherein the two orientations can be converted into each other by a rotation by 180°, in particular about an axis of rotation parallel to the optical axis 270 of the LED 200.

FIG. 34 illustrates the holding part 220' in semitransparent form, and FIG. 35 shows a corresponding exploded illustration.

Figure 36:
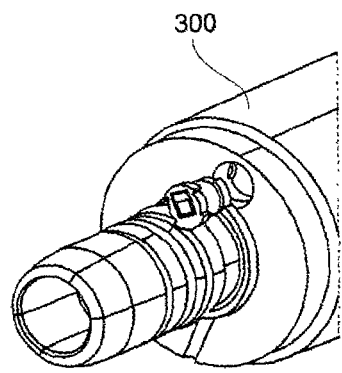
Figure 37:
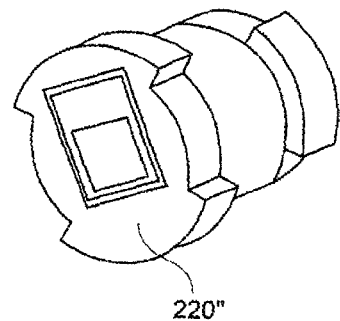
Figure 38:
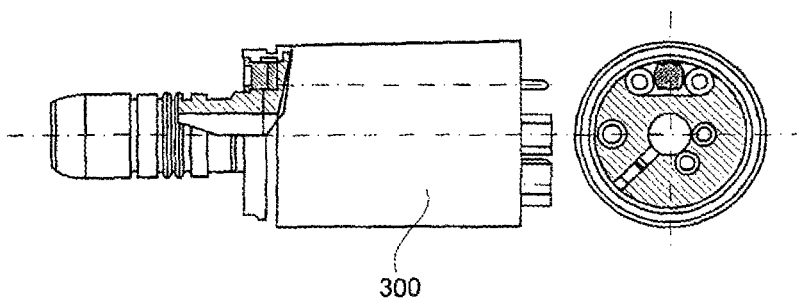

FIGS. 36 to 38 schematically depict an embodiment wherein the holding part 220″ can be inserted into the motor housing 300 in an axial direction.

Figure 39:
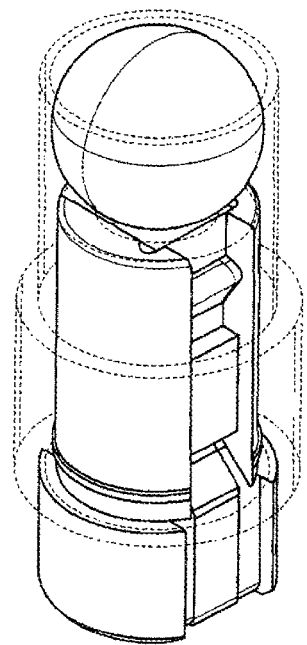
FIG. 39 shows a further variant of a holding part with a light source.
Figure 40:
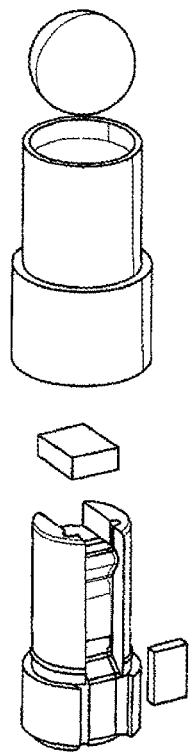
FIG. 40 shows a corresponding exploded illustration.

FIGS. 39 and 40 show further configurations of a holding element.

FIGS. 41 to 44 illustrate a further variant, with the holding part 220‴ and with a corresponding carrier element 210′. In this case, the schematic cross-sectional view in FIG. 42 shows alternatively designed contact pins 230′ embodied for making contact on correspondingly alternative contact areas 211′ of the holding part 220‴ or of the corresponding carrier part 210′. The contact areas 211′ are in this case arranged laterally with respect to the longitudinal axis L. In this case, therefore, contact is made at two opposite outer areas or outer edges of the carrier element 210′ or of the holding part 220‴, to be precise preferably by clamping between the two contact pins 230′. These contact pins 230′ can in turn be electrically conductively connected to corresponding contact rods 230, which are in turn preferably surrounded by the sheath element 6. In the case of such lateral contact-making, besides resiliently mounted contact pins, solid conductors embedded in plastic can also be used. The holding part 220‴ can in turn be designed as a "slide" and can be fixed by means of a securing element, for example in the form of a holding ring or some other locking element. This system enables simple installation and demounting by (i) releasing and removing the holding ring, (ii) radially pulling the slide, (iii) inserting a new LED and (iv) replacing the holding ring.

In this configuration, the illumination element or the holding part 220‴, in the case of contact being made with incorrect polarity, can be very simply separated from the motor housing 300, correspondingly rotated and inserted again in order to establish the correct polarity.

Therefore, it is possible to form an illumination element which includes the optical element 221, the LED 200 and the carrier element 210 or consists of these components. The illumination element can form a slide fixed in the motor housing 200. The slide and the motor housing 300 can be configured so that the slide can be inserted into the motor housing 300 in a manner rotatable by 180° about an axis.

The carrier element 210 can be a three-dimensionally injection-molded circuit carrier (3-D MID). In this case, the contact areas can be embodied as part of the conductor structure on side areas. The contact areas and conductors can have the layer construction CuNiAu or WoNiAu. The circuit carrier can be produced from or consist of ceramic (aluminum oxide or aluminum nitride). The circuit carrier can be formed from LTCC (low temperature cofired ceramic) as a multilayer. The circuit carrier can contain a metal core. The circuit carrier can contain means (shape, tongue-groove, lug-cutout), for orientation with respect to the optical system. The connection between optical system housing and circuit carrier can be implemented by means of snap-action connection or by means of adhesive-bonding connection. The housing can have grooves (capillaries) for distributing adhesive. The housing can have cutouts that can be used as an adhesive reservoir or replenishment reservoir. A cavity between LED circuit carrier and optical system housing can be filled with a transparent potting compound or with a transparent adhesive.

A further aspect of the invention relates to a coupling element of the electric motor arrangement, the coupling element being provided for connection to the handpiece.

Experiments have shown that the guide length at the coupling of handpiece/angular piece to the motor can be reduced without losses of function.

On the motor, the coupling pin is correspondingly shortened. In the handpiece and angular piece, the insertion depth (cutout for receiving the coupling pin) can be correspondingly shortened, or the handpiece and angular piece can be made correspondingly shorter.

A motor having a shortened coupling pin can at any time also be used with a handpiece/angular piece in an old embodiment. However, the ergonomic advantage arising from a shorter instrument does not take effect in this case. A handpiece and angular piece in a new embodiment cannot be operated in combination with a motor in an old embodiment (long coupling pin). The coupling pin strikes the angular piece internally and cannot be locked.

The following features of the known INTRAmatic coupling in accordance with ISO 3964 are maintained:

Via grooves and holes in the wall with the coupling pin, the media cooling air, spray air, spray water are supplied to the angular piece. For media separation (spray air/spray water) and sealing, O-rings are arranged between the individual exit openings on the circumference of the coupling pin. If necessary, water is prevented from being sucked back from the handpiece/angular piece into the supply line by a covering of the exit opening in the coupling pin by means of an O-ring. When spray water is conveyed, the O-ring lifts off and allows the spray water to flow to the processing site. If no conveying pressure is present, the O-ring closes off the exit opening and thus prevents water from being sucked back from the handpiece and angular piece into the motor and the supply line.

Locking/holding ring

Coupling of light into optical fiber rod

Securing against rotation/latching

The concept of the coupling in accordance with the invention is illustrated in greater detail with reference to FIGS. 45 and 46. FIG. 45 shows the coupling pin 310 in accordance with the prior art, in particular as part of the known INTRAmatic coupling. FIG. 46 shows the design with a correspondingly shortened coupling pin 310′. The rotor shaft is arranged to be mounted rotatably about the longitudinal axis L by two bearings 330, 331. The motor housing 300 surrounds the two bearings 330, 331 radially from outside with respect to the rotor shaft or the longitudinal axis L. Furthermore, a first balancing ring 320, a second balancing ring 321 and a permanent magnet 333 as part of the rotor can be discerned. Furthermore, a reverse suction stop 334 and a bearing shield 335 are designated. The rotor shaft engages with a claw 336 from inside into the coupling pin 310.

The configuration in accordance with FIG. 46 with the coupling pin 310′ shortened according to the invention differs from the configuration shown in FIG. 45 only in the length l of the coupling pin 310′.

In accordance with the prior art, the INTRAmatic coupling for handpieces and angular pieces according to ISO 3964 is screwed to an end side of a motor housing 300 of the electric motor arrangement. In this case, there is the risk of the two corresponding end faces of motor housing 300, on the one hand, and coupling element, on the other hand, not extending exactly in a planar fashion; this can have the effect that the coupling pin 310 in the mounted state has a significant inclination, which can subsequently lead to a declination of the attached handpiece. Moreover, ergonomic aspects such as weight and compact structural size are significant factors in dental drives.

Figure 47:
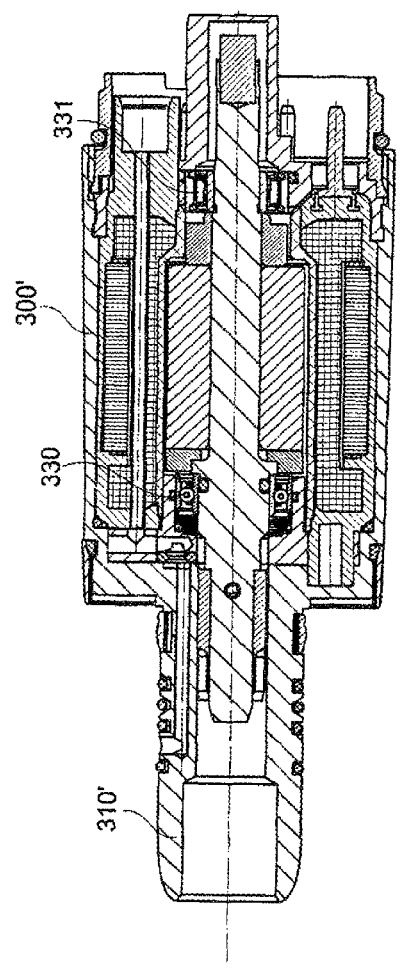
FIG. 47 shows a configuration wherein the motor housing and the coupling pin are embodied in one piece or in an integral fashion.
Figure 48:
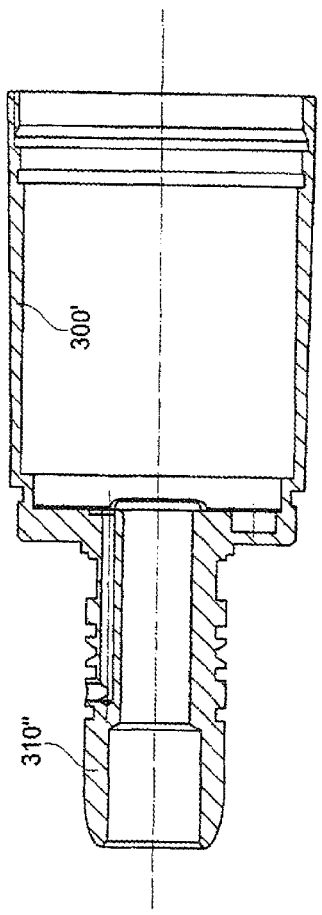
FIG. 48 shows the motor housing with the coupling pin separated.

The stated problem can be solved by virtue of the fact that—as is apparent for example from FIGS. 47 and 48—the motor housing 300′, which has, more particularly, as described, the two bearings 330 and 331 for the mounting of the rotor shaft, and the coupling element arranged on the electric motor arrangement in the form of the coupling pin 310" are embodied in one piece or integrally. In this way, the electric motor arrangement can, more particularly, also be made shorter and lighter. The declination is minimal since the coupling element or the coupling pin 310" and the motor housing 300' can be produced in one set-up. An incorrect position possibly present as a result of the shortened coupling pin 310" is thus reduced.

Furthermore, the sound coupling from the electric motor arrangement to the handpiece is reduced, and emission by the instrument is reduced. Consequently, with the electric motor arrangement with the shortened coupling pin 310" and the integral embodiment of motor housing 300' and coupling element, the noise that arises during operation in conjunction with the attached or coupled handpiece can be made quieter.

Ultimately, a short, sterilization-resistant dental motor is correspondingly provided which is distinguished by the following characteristic properties:
- the use of a light source based on SMD-LED or LED as semiconductor chip;
- the shortening of the INTRAmatic coupling to 20 to 25 mm
- a stator encapsulated by injection molding in a hermetically sealed manner with integrated medium tubes and integrally formed connection sockets
- the embodiment of the stator winding as a coil segment winding instead of H winding or delta
- the forming of the winding overhang with an opening for media tubes.

The invention claimed is:

1. An electric motor arrangement for a medical handpiece, comprising
   a coupling pin configured to connect to the handpiece,
   a rotor with a rotor shaft having a shaft end extending into the coupling pin,
   a stator arranged around the rotor with respect to the rotor shaft,
   a medium tube for guiding a medium through the electric motor arrangement,
   a sheath element formed by encapsulation by injection molding, the sheath element, with respect to the rotor shaft, tightly surrounding a radially outward surface of both the stator and the medium tube in a closed manner,
   a claw disposed on the shaft end extending into the coupling pin;
   wherein the claw is configured to deliver torque from the rotor shaft to the medical handpiece,
   the stator has a stator winding, and a first part of the stator winding, with respect to the rotor shaft, is arranged radially outside the medium tube, and a second part of the stator winding radially inside the medium tube, and
   electrical conductors configured to make electrical contact with the stator, the electrical conductors extending through the stator winding in an axial direction and extending outwardly from the sheath element.

2. The electric motor arrangement as claimed in claim 1, wherein the sheath element extends beyond the stator on both sides as viewed along the rotor shaft and surrounds the medium tube in each case directly in a ring-shaped manner on both sides of the stator.

3. The electric motor arrangement as claimed in claim 2, wherein an introduction funnel for the medium tube is formed by the sheath element.

4. The electric motor arrangement as claimed in claim 1, wherein the stator has a tubular coil former, which, with respect to the rotor shaft, forms a radially inner boundary of the stator, wherein the sheath element is arranged in a manner directly adjoining the coil former.

5. The electric motor arrangement as claimed in claim 4, wherein the coil former has a holding element for fixing the medium tube.

6. The electric motor arrangement as claimed in claim 5 wherein the holding element is a latching element.

7. The electric motor arrangement as claimed in claim 5, wherein the holding element comprises a plurality of radially outwardly extending holding elements for fixing the medium tube.

8. The electric motor arrangement as claimed in claim 7, wherein each of the holding elements comprises a pair of radially outwardly extending walls, the medium tube being seated between the radially outwardly extending walls of at least one of the holding elements.

9. The electric motor arrangement as claimed in claim 4, wherein the stator has a tubular return path element, and the coil former has an abutment element for positioning the return path element along the rotor shaft and/or a centering element for centering the return path element with respect to the rotor shaft.

10. The electric motor arrangement as claimed in claim 4, wherein the stator has a tubular return path element surrounding the tubular coil former.

11. The electric motor arrangement as claimed in claim 10, wherein the coil former has a plurality of radially outwardly extending holding elements for fixing the medium tube and centering the tubular return path element.

12. The electric motor arrangement as claimed in claim 1, wherein the sheath element is formed of PEEK, PPS, LCP, PAI, PPSU, PSU, or PES.

13. The electric motor arrangement as claimed in claim 1, wherein the medium comprises water.

14. The electric motor arrangement as claimed in claim 13, wherein the medium further comprises air.

* * * * *